(12) United States Patent
Bukstein et al.

(10) Patent No.: US 11,510,849 B2
(45) Date of Patent: *Nov. 29, 2022

(54) ROTARY PILL DISPENSER AND METHOD OF USE

(71) Applicant: Zig Therapeutics, Inc., Indianapolis, IN (US)

(72) Inventors: Don A. Bukstein, Fitchburg, WI (US); Gary C. Steven, New Berlin, WI (US); Joseph C. Steven, Wauwatosa, WI (US)

(73) Assignee: Zig Therapeutics, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/078,904

(22) Filed: Oct. 23, 2020

(65) Prior Publication Data

US 2021/0038477 A1 Feb. 11, 2021

Related U.S. Application Data

(60) Continuation of application No. 16/243,905, filed on Jan. 9, 2019, now Pat. No. 10,849,829, which is a
(Continued)

(51) Int. Cl.
*A61J 7/04* (2006.01)
*A61J 7/00* (2006.01)
(Continued)

(52) U.S. Cl.
CPC ........... *A61J 7/0076* (2013.01); *A61J 7/0418* (2015.05); *G01C 19/00* (2013.01); *G01P 15/00* (2013.01);
(Continued)

(58) Field of Classification Search
USPC .................................................. 700/231–244
See application file for complete search history.

(56) References Cited

U.S. PATENT DOCUMENTS 2,199,242 A * 4/1940 Ladd ....................... A24F 15/04
221/87
4,127,190 A 11/1978 Sunnen
(Continued)

OTHER PUBLICATIONS

International Search Report and Written Opinion of the International Searching Authority dated Jul. 14, 2016, for International Appln. No. PCT/US16/01676 filed Feb. 5, 2016, 16 pages.

*Primary Examiner* — Timothy R Waggoner
(74) *Attorney, Agent, or Firm* — Boardman & Clark LLP

(57) ABSTRACT

An automated medication dispenser system is disclosed. The system includes a dispenser device comprising a medication dispensing and storage module, a dispensing drive and control mechanism, and a communications interface. A third party communications host is in communication with the dispenser device, and has administration software with executable instructions for control of the dispensing drive and control mechanism to dispense medication from the medication dispensing and storage module. The communications interface is in communication with the third party communications host.

10 Claims, 12 Drawing Sheets

Related U.S. Application Data division of application No. 15/016,757, filed on Feb. 5, 2016, now Pat. No. 10,201,478.

(60) Provisional application No. 62/112,522, filed on Feb. 5, 2015.

(51) Int. Cl.

| | |
|---|---|
| *G01C 19/00* | (2013.01) |
| *G01P 15/00* | (2006.01) |
| *G05B 15/02* | (2006.01) |
| *G16H 20/13* | (2018.01) |
| *A61J 1/14* | (2006.01) |

(52) U.S. Cl.
CPC ............. *G05B 15/02* (2013.01); *G16H 20/13* (2018.01); *A61J 1/1412* (2013.01); *A61J 2200/30* (2013.01)

(56) References Cited

U.S. PATENT DOCUMENTS

| | | |
|---|---|---|
| 4,813,173 A | 3/1989 | Abbotoy |
| 5,522,525 A | 6/1996 | McLaughlin et al. |
| 5,810,198 A | 9/1998 | Townsend |
| 7,108,153 B2 | 9/2006 | Wood |
| 7,341,145 B2 | 3/2008 | Vandenbroek et al. |
| 8,483,872 B2 * | 7/2013 | Ratnakar ............... A61J 7/0076 700/240 |
| 9,572,748 B2 * | 2/2017 | Lim ......................... A61J 1/03 |
| 9,901,515 B2 * | 2/2018 | Roberts ................. A61J 7/0463 |
| 10,201,478 B2 * | 2/2019 | Bukstein ............... A61J 7/0418 |
| 10,849,829 B2 * | 12/2020 | Bukstein ............... A61J 7/0076 |
| 2005/0172964 A1 | 8/2005 | Anderson et al. |
| 2007/0156282 A1 | 7/2007 | Dunn |
| 2007/0186923 A1 * | 8/2007 | Poutiatine ......... A61M 15/0083 128/200.14 |
| 2008/0203107 A1 | 8/2008 | Conley et al. |
| 2009/0020549 A1 | 1/2009 | Lyndegaard et al. |
| 2009/0127157 A1 | 5/2009 | Costa et al. |
| 2010/0253476 A1 | 10/2010 | Poutiatine |
| 2011/0170655 A1 | 7/2011 | Yuyama |
| 2012/0003928 A1 * | 1/2012 | Geboers ................ A61J 7/0445 455/41.1 |
| 2014/0244033 A1 | 8/2014 | Ucer et al. |
| 2014/0277702 A1 | 9/2014 | Shaw |
| 2015/0278479 A1 | 10/2015 | Ervin |
| 2015/0291344 A1 * | 10/2015 | MacVittie ............. A61J 7/0418 221/13 |

\* cited by examiner

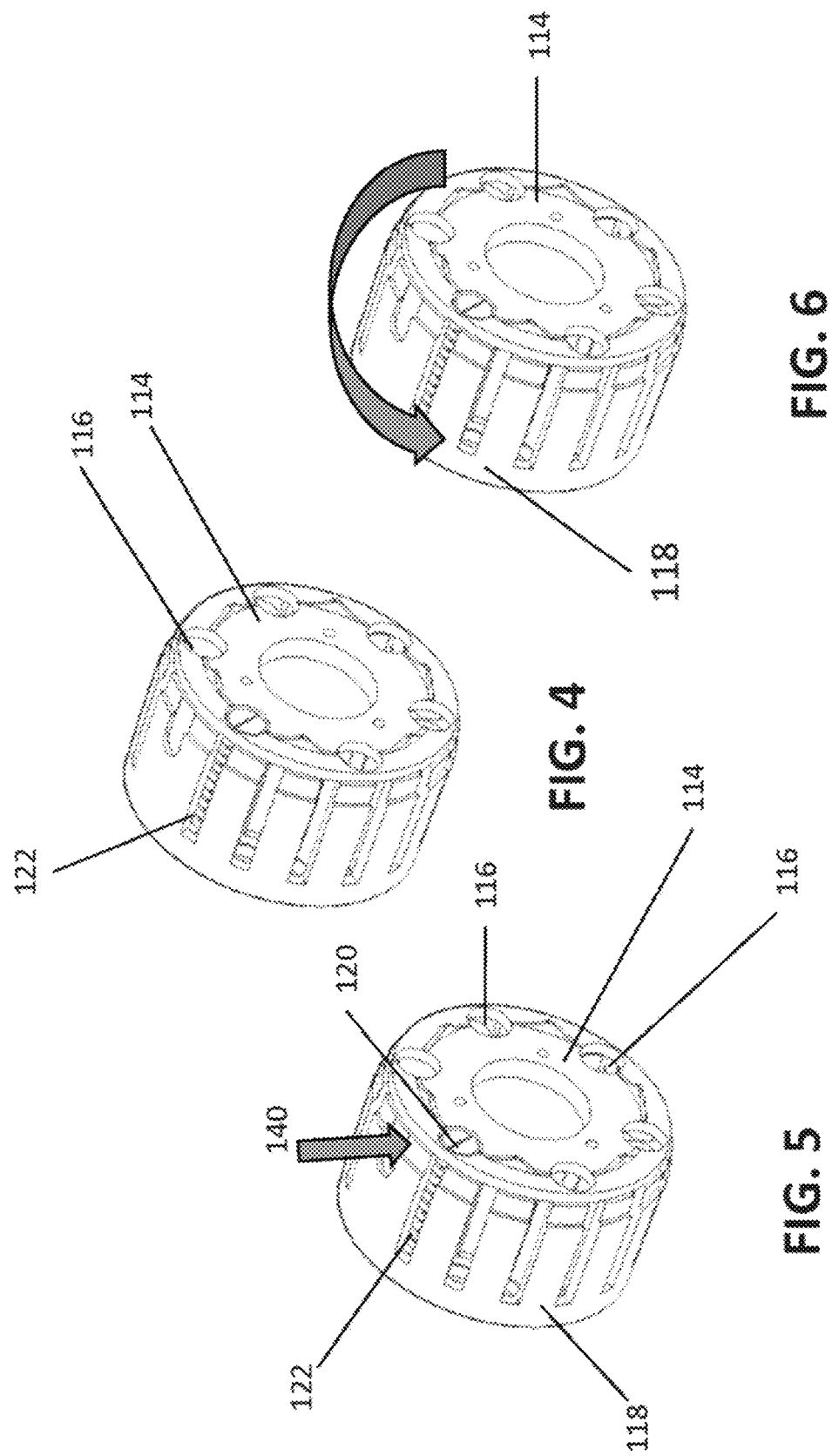

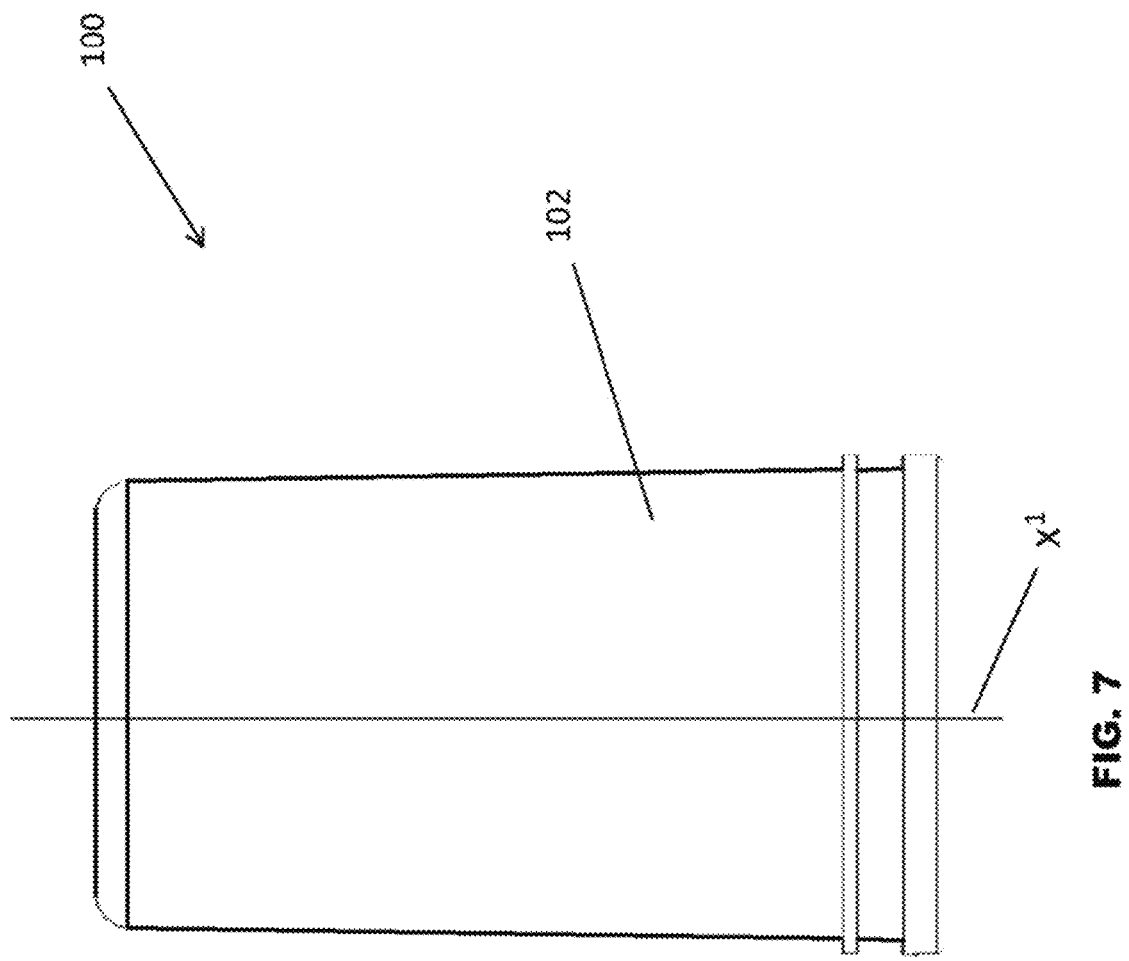

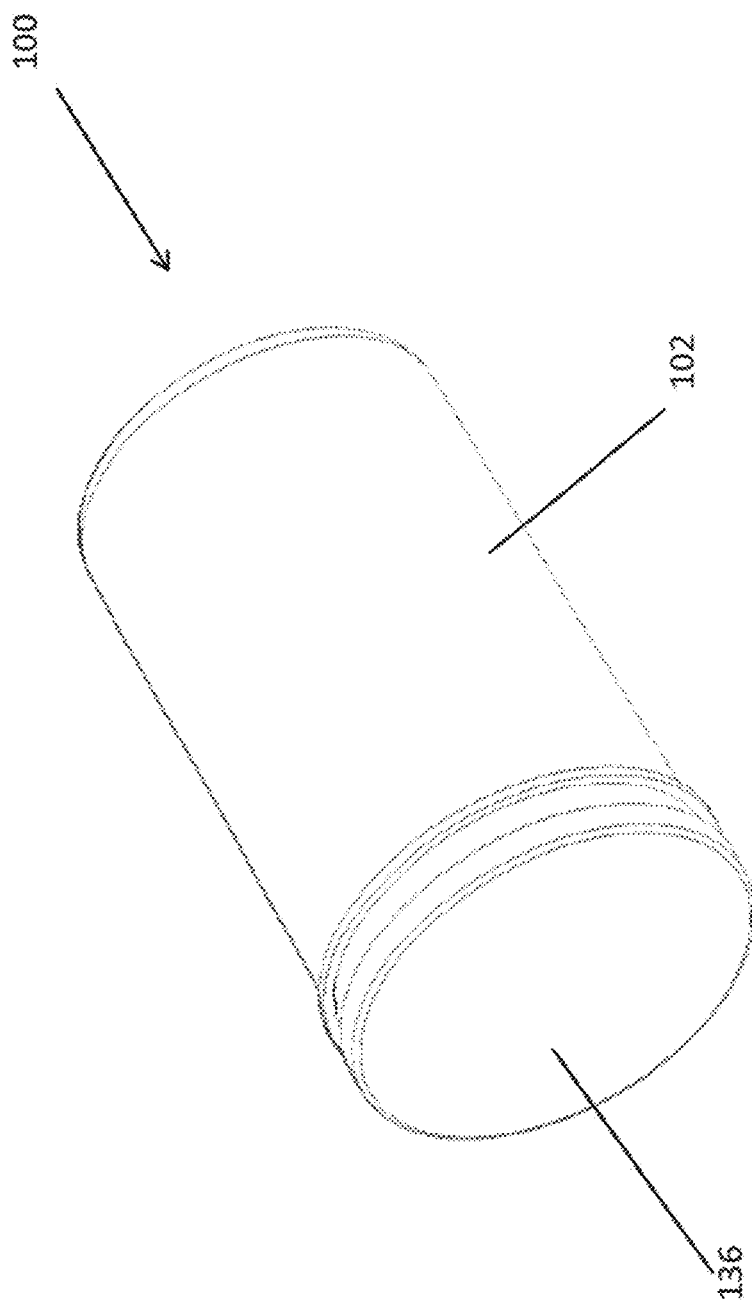

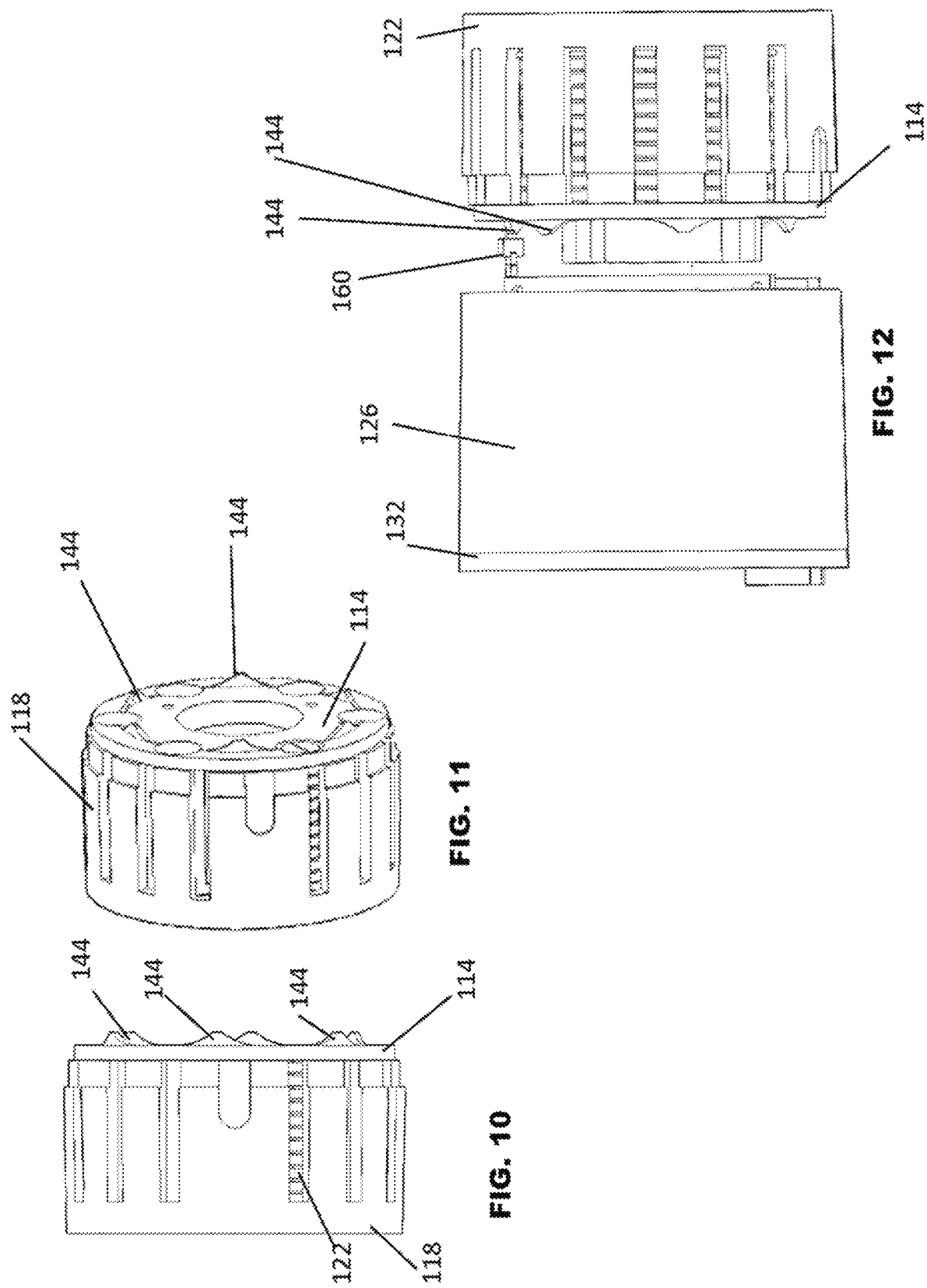

ROTARY PILL DISPENSER AND METHOD OF USE

CROSS-REFERENCE TO RELATED APPLICATIONS

This application claims priority as a continuation of U.S. patent application Ser. No. 16/243,905, filed Jan. 9, 2019, now U.S. Pat. No. 10,849,829; which is a division of U.S. patent application Ser. No. 15/016,757, filed Feb. 12, 2019, now U.S. Pat. No. 10,201,478; which claims benefit of United States Provisional Patent Application, Serial No. 62/112,522, filed Feb. 5, 2015, entitled "Dispenser for Determining Use of Oral Steroids," the entire contents of each of which are hereby incorporated by reference.

FIELD

The present inventions relate to the field of medication containers and dispensers. The present inventions more specifically relate to the field of medication dispensers for determining use of oral steroids.

BACKGROUND

It has been shown that patients with a history of three or more bursts of oral steroids for asthma exacerbations are at increased risk of future exacerbation. In the United States, national guidelines recommend assessing oral corticosteroid use as a marker of asthma severity and control. The history of asthma exacerbations is an important component of the risk domain of asthma control, which weighs heavily in treatment decisions. However, to date, determining the number of bursts of oral steroids has been difficult and is often inaccurate.

Most physicians, including allergists, assess the frequency of prior asthma exacerbations by taking a history from the patient of the number of times the patient has taken OCS (oral corticosteroid) bursts. Patient history, however, has been found to miss as many as 58% of patients who have had three or more exacerbations in the past year. Pharmacy refill records can also be used to determine whether patients had three or more bursts of oral steroids and are believed to be more accurate. However, few physicians use computerized data from pharmacies to determine the number of OCS bursts used for asthma exacerbations.

Pharmacy data should be considered as part of the clinical assessment of patients with difficult-to-treat asthma. Identifying these patients can result in additional interventions that would further reduce the patent's risk of further exacerbations. Therefore, an improved means to determine and use pharmacy data on the use of oral medication, such as steroids, is needed.

In addition to the foregoing, a need exists for monitoring and control of the dispensation of medication.

SUMMARY

Accordingly, a medication container and dispenser for determining use of oral steroids and other medications is provided, as well as a method for using same.

More particularly, an automated pill dispenser is disclosed. The automated pill dispenser uses a series of mechanical features, coupled with electrical and electronic controls, communications hardware and monitoring software to dispense controlled quantities of medication. While dispensing action may be patient driven, the device remains under the control and monitoring of a remote administrator, and in some examples may be controlled and monitored at all times while powered up. Remote monitoring of the device's actuation, dosage and frequency of allowable use is monitored and controlled by an administration portal. In addition to monitoring of one or more, or all of the above features, two-way communication between the device and the administrator via a cellular or other wireless signal may also be provided to allow an administrator the ability to adjust any of the device parameters remotely and receive real-time feedback on its use.

Thus, an automated medication dispenser system is disclosed. The system includes a dispenser device comprising a medication dispensing and storage module, a dispensing drive and control mechanism, and a communications interface. A third party communications host is in communication with the dispenser device, and has administration software with executable instructions for control of the dispensing drive and control mechanism to dispense medication from the medication dispensing and storage module. The communications interface is in communication with the third party communications host.

A medication dispenser is also disclosed. The dispenser includes a dispenser housing. The housing contains a microprocessor which is linked to a gear motor, wherein the gear motor is coupled to a pinion gear, and the pinion gear is engaged with an internal gear. The housing also contains a medication dispensing plate coupled to the internal gear, wherein as the gear motor actuates; the pinion gear rotates which rotates internal gear and the dispensing plate. The housing further contains a stationary medication holder, with medication stores arranged in a circular configuration about the dispensing plate's axis of rotation, wherein spring pressure is exerted on a base of each medication store forcing medication therein in the direction of the dispensing plate, such that a dose of medication is forced into a vacant aperture in the dispensing plate.

A method for control and monitoring the dosing of medication is also provided. The method includes connecting a dispenser device with a third party host, and once paired, automatically communicating the availability of a dose of medication to the dispenser device. Following loading of the dose of medication, the loading of additional doses of medication is restricted without additional instructions. Request for further instruction with physician input is sent to a third party host. Upon receipt of the instructions, dosing instructions are sent to the dispenser device. The method also includes querying whether a dispense button has been depressed and operating the dispenser device to deliver a predetermined quantity of medication according to the dosing instructions.

These and other features and advantages of devices, systems, and methods according to this invention are described in, or are apparent from, the following detailed descriptions of various examples of embodiments.

BRIEF DESCRIPTION OF DRAWINGS

Various examples of embodiments of the systems, devices, and methods according to this invention will be described in detail, with reference to the following figures, wherein:

FIG. 4 is a perspective view of the dispensing plate and medication holder for use with the dispenser device shown in FIG. 1, according to one or more examples of embodiments.

FIG. 5 is a perspective view of the dispensing plate and medication holder for use with the dispenser device shown in FIG. 1, according to one or more examples of embodiments, identifying a pill in a cavity or aperture of the dispensing plate.

FIG. 6 is a perspective view of the dispensing plate and medication holder for use with the dispenser device shown in FIG. 1, according to one or more examples of embodiments, showing a pill in a cavity or aperture of the dispensing plate, and notation reflecting rotation of the dispensing plate.

FIG. 7 is a side elevation view of the dispenser device of FIG. 1, showing the device in a vertical orientation and the vertical axis (x').

FIG. 9 is an alternative perspective view of the dispenser device of FIG. 1, according to one or more examples of embodiments.

FIG. 10 is a side elevation view of the dispensing plate and medication holder for use with the dispenser device shown in FIG. 1, according to one or more examples of embodiments, showing the cycle count cam lobe.

FIG. 11 is a perspective view of the dispensing plate and medication holder for use with the dispenser device shown in FIG. 1, according to one or more examples of embodiments, showing the cycle count cam lobe.

FIG. 12 is a partial side elevation view of the dispensing plate and medication holder, battery housing, and retaining plate for use with the dispenser device shown in FIG. 1, according to one or more examples of embodiments, showing the cycle count cam lobe and cycle count switch.

It should be understood that the drawings are not necessarily to scale. In certain instances, details that are not necessary to the understanding of the invention or render other details difficult to perceive may have been omitted. It should be understood, of course, that the invention is not necessarily limited to the particular embodiments illustrated herein.

DETAILED DESCRIPTION

Referring to the Figures, one or more examples of a dispenser, a mechanism by which the dispenser operates, and a method of operation of the dispenser are provided. In particular, the Figures illustrate a rotary pill dispenser and more specifically, an automated pill dispenser 100 according to one or more examples of embodiments. Generally, the dispenser 100 is able to identify and count the number of pills 120 or other medication dispensed by the device, as well as be programmed to identify the next dose time and amount. The medication is dispensed according to a mechanical or electronic metering system. As a result, the dispenser 100 shown herein is able to determine the use of medication (such as but not limited to oral steroids, among other medications), and may be used to communicate and control the amount used to a patient, physician, and others. In addition, the dispenser 100 may be equipped to send a signal to a cell phone or other portable computing device. In one or more examples of embodiments, the dispenser is replaceable. In alternative examples of embodiments, the dispenser is refillable.

Figure 1:
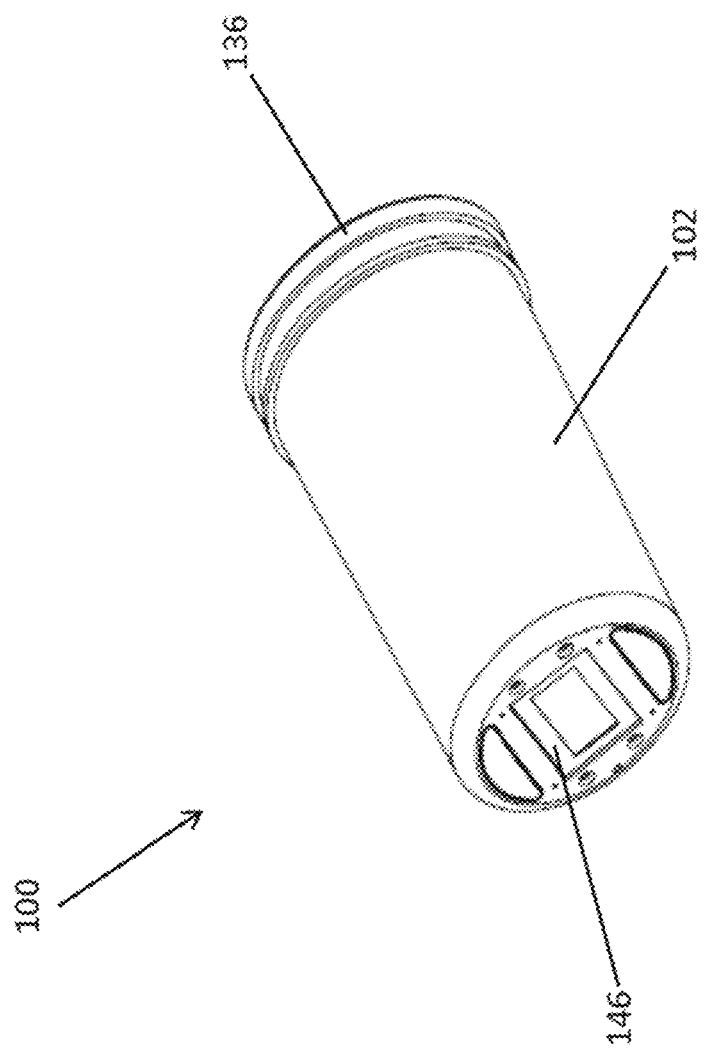
FIG. 1 is a perspective view of a dispenser device according to one or more examples of embodiments.
Figure 2:
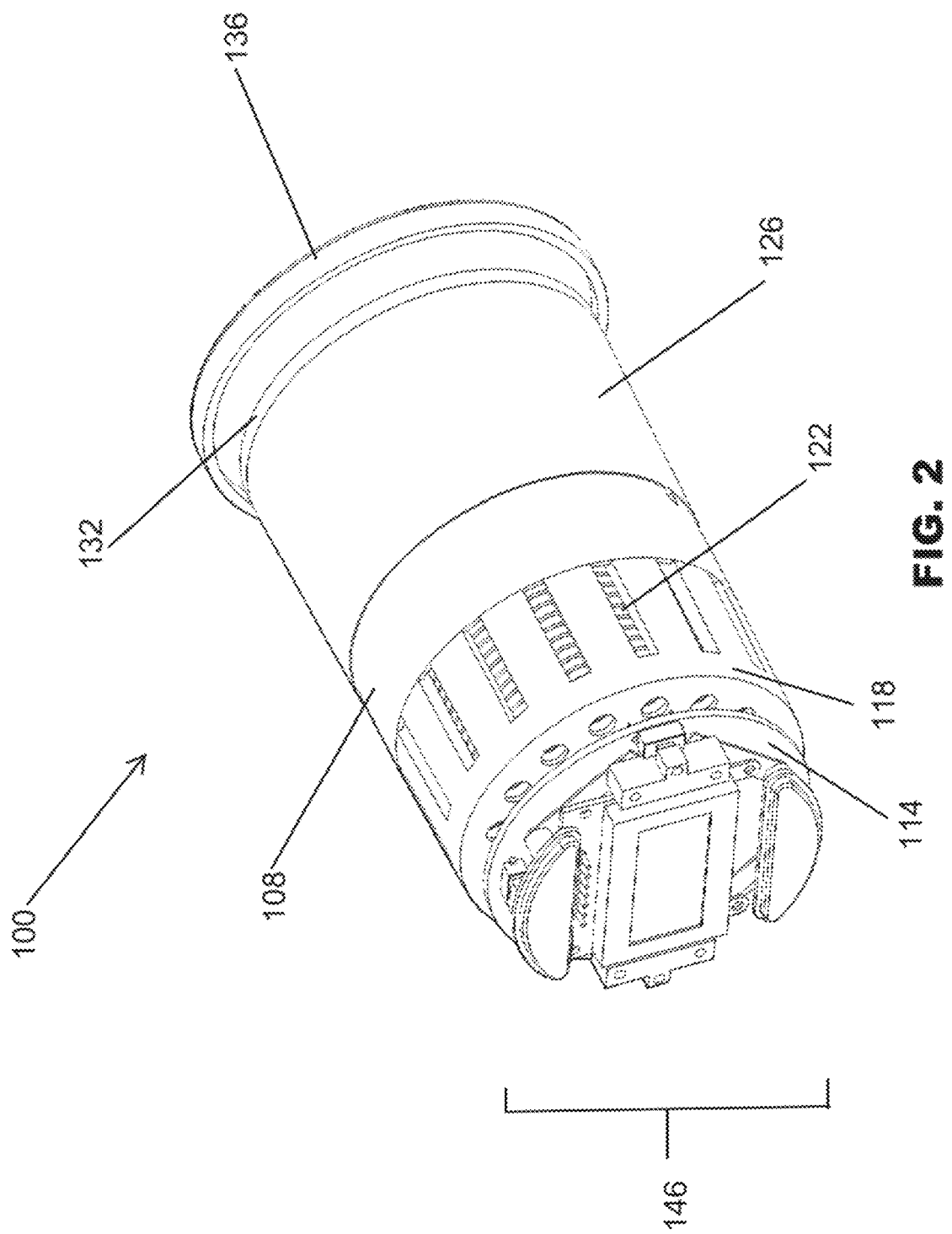
FIG. 2 is a cut-away perspective view of the dispenser device shown in FIG. 1, with the dispenser housing removed.
Figure 3:
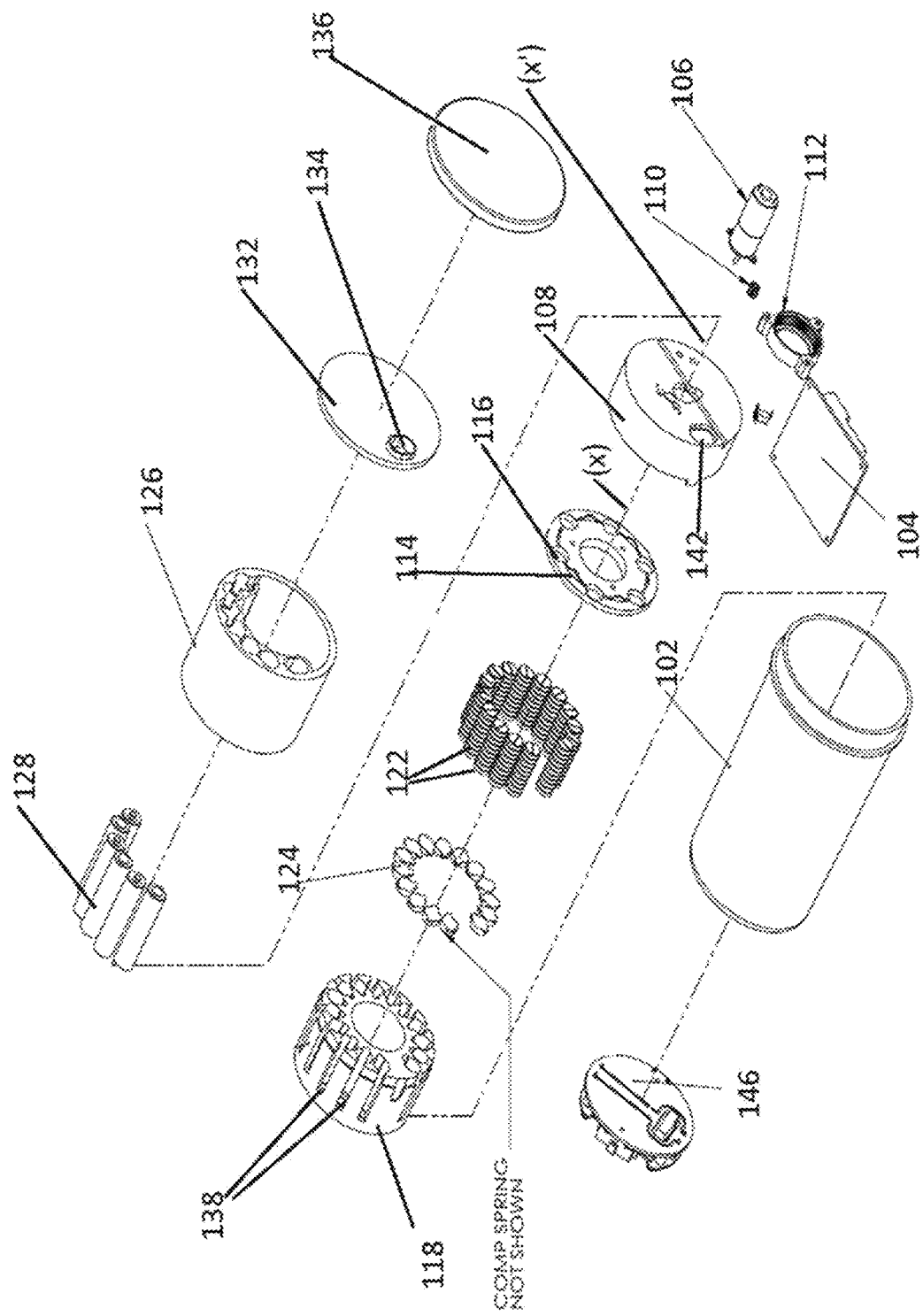
FIG. 3 is an exploded view of the dispenser device according to one or more examples of embodiments.

Generally, the automated pill dispenser 100, shown in FIGS. 1-3, consists of three major onboard sub-assemblies and two remotely located support components. Onboard components may include, but are not limited to, a dispensing and storage module, a dispensing drive and control mechanism, and a communications interface. Remote components may include, but are not limited to a third party communications host and administration software.

In one or more examples of embodiments as further described herein, the device 100 contains all of the hardware and localized control software required to perform independent dispensing operations. Functions are further enhanced by the communication and control application which may reside on a third party host (such as, but not limited to, a cell phone or other Bluetooth enabled, or near field communication enabled equipment).

According to one or more examples of embodiments, various onboard components are provided, including, for example a dispensing and storage module, as well as a dispensing drive and control mechanism. In particular, referring to FIGS. 1-3, the dispenser device 100 contains a number of components within or on a dispenser housing 102. Secondly, the operations of the dispenser device 100 are monitored or controlled by a microprocessor 104 contained within the housing 102. The microprocessor 104 is linked to a motor 106 which, through various linkages and gears discussed in further detail hereinbelow, forms the dispensing assembly.

In particular, the microprocessor 104 is in communication with, and facilitates or controls operation of a DC gear motor 106. While a DC gear motor 106 is specifically described for purposes of example, variations thereon accomplishing the same purposes would not depart from the overall scope of the present invention. A motor mounting flange 108 carries the gear motor 106. The gear motor 106 is coupled to a pinion or spur gear 110. The pinion gear 110 is engaged with an internal spur gear or internal gear 112. The internal gear 112 is coupled to the pill dispensing plate 114. Consequently, as the gear motor 106 actuates, pinion gear 110 rotates, which, in turn, rotates internal gear 112 and the dispensing plate 114. The gears described herein may be toothed gears or other gears known in the art suitable for accomplishing the purposes provided.

Referring to FIGS. 2-6, the stationary pill holder 118 contains a pre-loaded quantity of medication, illustrated in FIG. 4 in pill form 120. Medication or pills 120 are stored in a silo configuration 122. According to one or more examples of embodiments, the pill holder 118 is sized to precisely accept and contain the particular pills 120 to be dispensed. Pill silos 122 are arranged in a circular configuration about the dispenser plate's axis of rotation (x) which may be co-axial with the dispenser device's vertical axis (x') (see FIGS. 3, 7).

In one or more examples of embodiments, a compression spring (not shown) and spring seat 124 are located at the base one or more, and preferably at the base of each pill silo 122. As a result, spring pressure is exerted on the base of each pill silo 122 forcing an entire column of pills 120 in the direction of the dispensing plate 114. Spring force (assisted by gravity) is provided to insert a dose of medication (e.g., a pill 120) into a vacant cavity or aperture 116 in the dispensing plate 114. Once an aperture or cavity is populated, the resident medication or pill 120 serves as a stop which inhibits additional silos 122 from loading into that particular aperture or cavity (see FIGS. 4-6).

Figure 8:
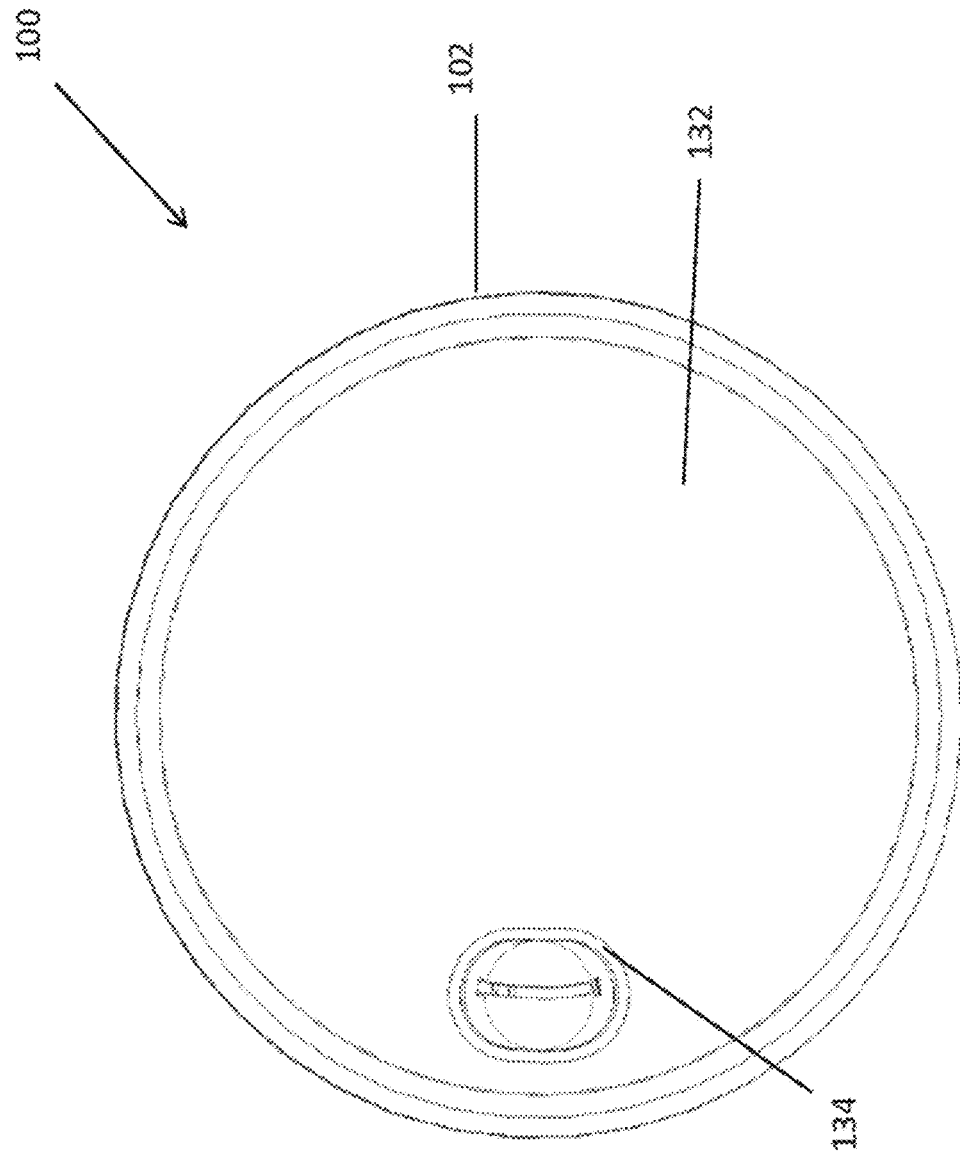
FIG. 8 is a bottom plan view of the dispenser device of FIG. 1, with the dispenser cap removed, showing the longitudinal cavity or aperture for medication dispensation.
Figure 13:
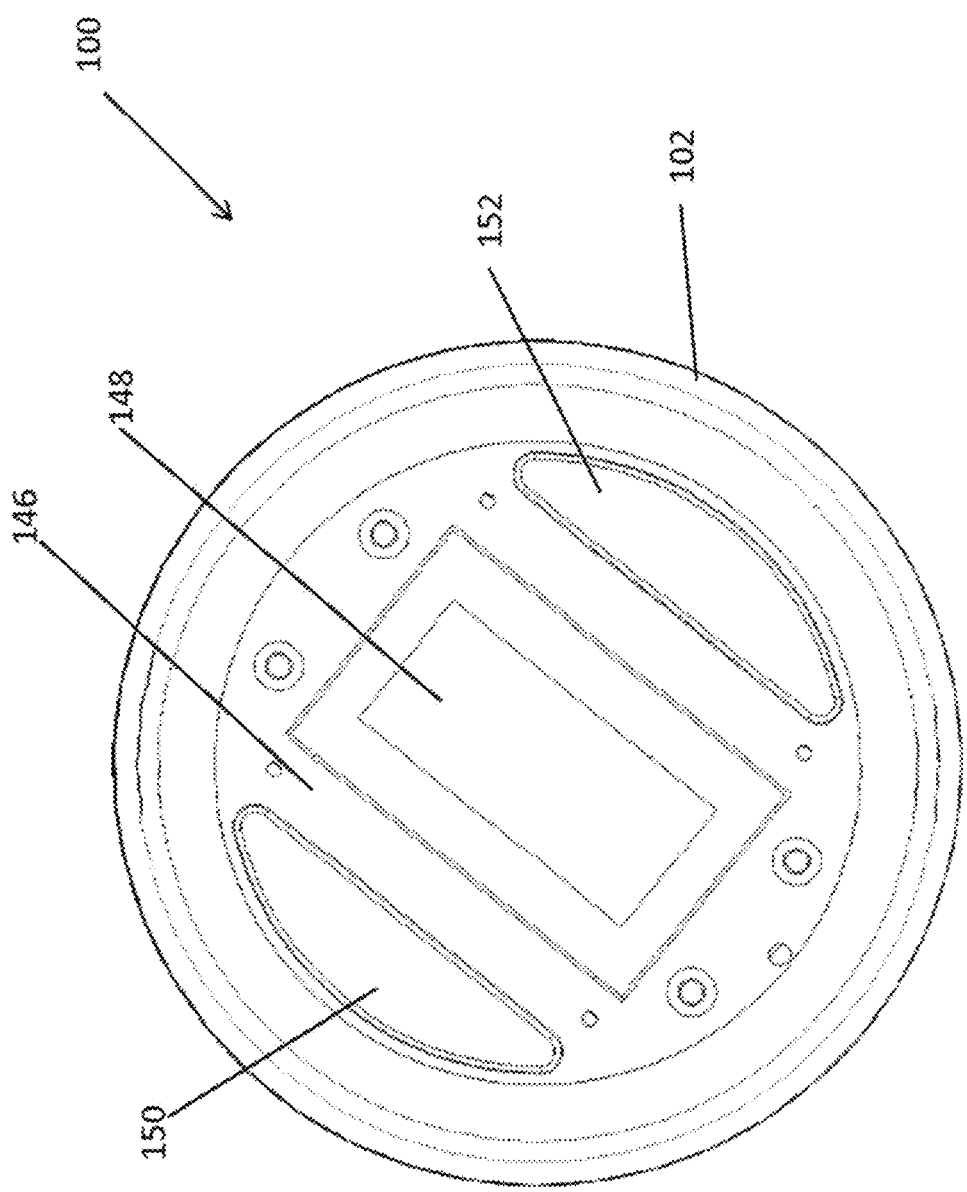
FIG. 13 is a top plan view of the dispenser device of FIG. 1, according to one or more examples of embodiments, showing the communication interface.
Figure 14:
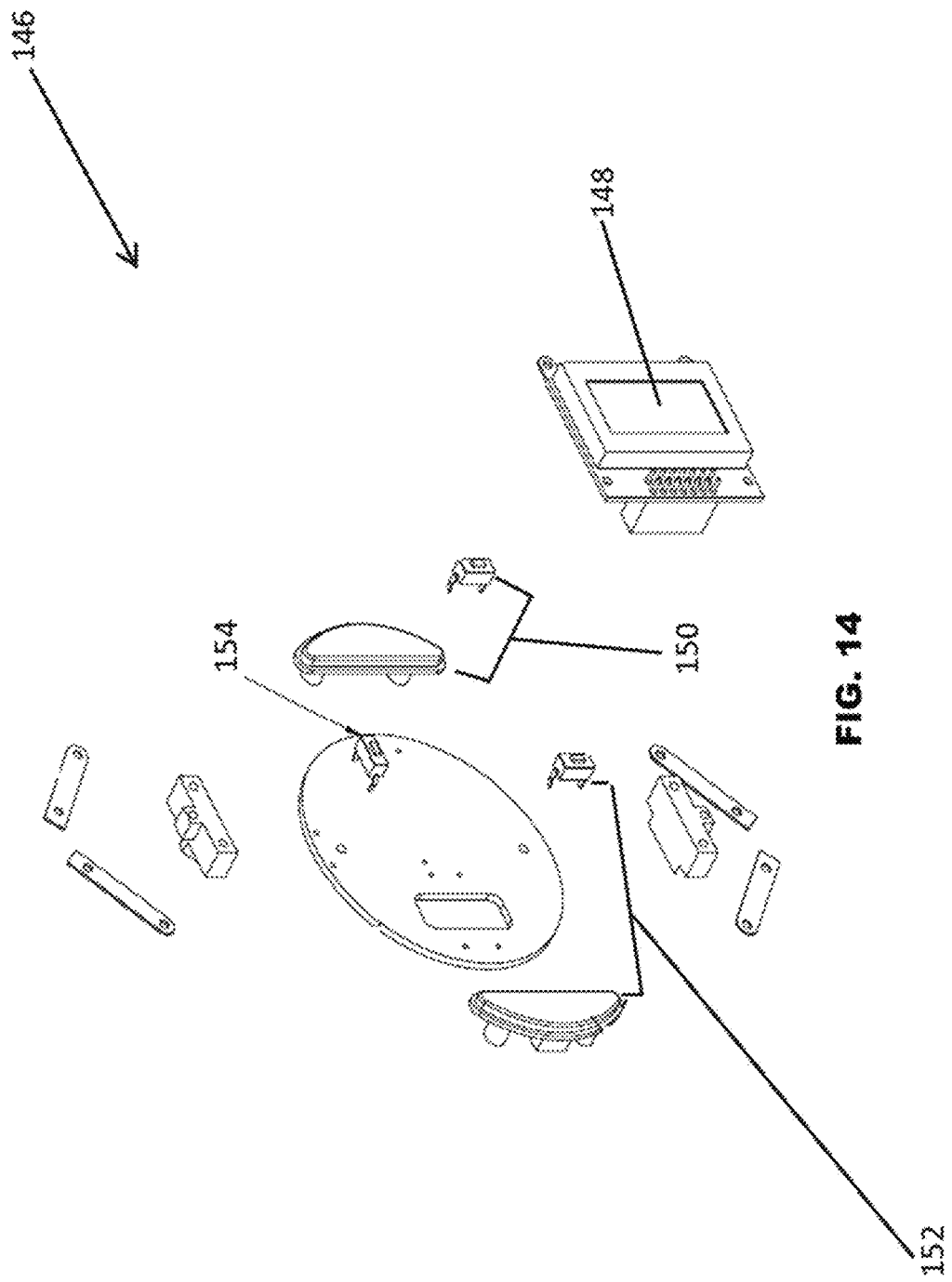
FIG. 14 is an exploded view of the communication interface of FIG. 13, for use with the dispenser device in one or more examples of embodiments.

In addition to the above described components, within the dispenser housing 102 is a battery housing 126, which holds, for example, a battery cell 128 and a cycle count switch 160 (see FIG. 12). The battery cell 128 may be an onboard rechargeable 7.2 VDC battery pack. However, variations thereon would not depart from the overall scope of the present invention, such as but not limited to one or more replaceable alkaline or lithium batteries. The battery cell 128 may be electrically coupled to the microprocessor 104 to provide power to the microprocessor 104. The cycle count switch 160 is also in communication with the microprocessor 104 to convey or count the dispensing action of the device. Referring to FIGS. 3 and 8, the battery housing 126 also may include an aperture or hole or cavity, such as a feed chute 130 extending therethrough and arranged or aligned for passage of medication (e.g., a pill 120). A retaining plate 132, also including an aperture or hole or cavity 134 which is aligned with the feed chute 130, is provided adjacent to the battery housing 126. Referring to FIGS. 3 and 9, a dispenser cap 136 may also be provided which couples to the dispenser housing 102 to enclose the components of dispenser described herein. In one or more examples of embodiments, the dispenser cap 136 is removable.

Referring to FIGS. 4-6, the dispensing plate 114 contains a series of cavities or holes or apertures 116 that may be rotated to momentarily align with cavities 138 in a pill holder 118 (e.g., as the dispensing plate 114 rotates). The dispensing plate 114 is rotatable to align the plate's aperture or cavity 116 with a pill silo 122. A pill or dose of medicine 120 in the plate's aperture 116, i.e., the populated cavity, prevents additional pills 120 from being loaded as the dispensing plate 114 is rotated about the respective stationary pill silos 122. In one or more examples of embodiments, a populated aperture or cavity 140 (e.g., containing a resident pill 120) is rotatable into alignment with a hole or aperture 142 located in the motor mounting flange 108 (see FIGS. 3, 8). The hole or aperture geometry of the internal components of the dispenser allow the pill to fall freely through the motor mounting flange 108 and continue through the feed chute 130 located in the battery housing 126, finally passing through an aperture 134 in the retaining plate 132 and coming to rest in a chamber located between and defined by the retaining plate 132 and the dispenser cap 136. Referring to FIGS. 10-12, in one or more examples of embodiments, the cycle count cam lobe 144 is provided which both engages the cycle count switch 160 and may further assist the evacuation of the pill through the motor mounting flange 108 as it passes through the center of the longitudinal cavity (formed by the various apertures and feed chute) during the rotation cycle.

Accordingly, the foregoing describes a medication dispenser. Generally, the medication dispenser includes a dispenser housing containing a microprocessor which is linked to a gear motor, wherein the gear motor is coupled to a pinion gear and the pinion gear is engaged with an internal gear. A medication dispensing plate is coupled to the internal gear, wherein as the gear motor actuates; the pinion gear rotates, which rotates internal gear and the dispensing plate. A stationary medication holder, with medication stores arranged in a circular configuration about the dispensing plate's axis of rotation, is also provided. Spring pressure is exerted on a base of each medication store, forcing medication therein in the direction of the dispensing plate, such that a dose of medication is forced into a vacant aperture in the dispensing plate. The stationary medication holder may contain a pre-loaded quantity of medication. For example, the medication dispenser may contain one or more pills stored in one or more silo configurations. In one or more examples of embodiments, the dispensing plate contains a series of apertures that, when the dispensing plate rotates, momentarily align with medication stores in the medication holder. A longitudinal cavity extends from the medication holder to a delivery end of the medication dispenser for passage of medication. A dispenser cap coupled to the dispenser housing. The medication dispenser may also have a battery cell within the dispenser housing. Likewise, as discussed further herein, the dispenser housing has a communications interface, and in some examples of embodiments, the microprocessor has a wireless communications module. A cycle count switch and cam lobe are also provided to count and relay or convey the actions (e.g., dispensing actions) of the dispenser.

In one or more examples of embodiments, the material(s) of the dispenser device 100 may be formed of a durable material. In one or more further examples of embodiments, the material(s) may be formed of a sterile material, or a material suitable for the containment and storage of and/or stability of medication. In one or more particular examples of embodiments, components herein may be composed of a plastic or polymeric material. Combinations of materials may also be acceptable, such as but not limited to, a motor with one or more metal or stainless steel gears and a polymeric housing. Various sealants and joint seals known in the art may also be used without departing from the overall scope of the present invention.

In various examples of embodiments, one or more of the dispenser device components are formed by molding and subsequently assembled in the linkages described herein. Likewise, in one or more examples of embodiments, the dispensing device or pill holder may be provided with an appropriate environmental seal which maintains the integrity and/or stability of the medication contained therein.

Referring to FIGS. 1-2 and 13-14 a communication interface 146 may be provided on or accessible through the housing 102. More specifically, the dispensing device 100 includes a face or surface containing a viewing or communication screen 148 and one or more interface buttons 150, 152 in communication with the microprocessor 104. In particular, the device has a screen 148 or communication window, such as an LCD screen 148, which may display messages to a user (e.g., a patient) and may accept commands. Variations thereon may also be acceptable such as, but not limited to, an LED screen. In addition, the dispenser device 100 has a momentary contact or switch 154, or more than one such contact or switch. For example, a discrete momentary contact 154 may "power on" the device. As indicated, the device also contains one or more additional control or function buttons or switches or combinations thereof. For example, two color coded buttons 150, 152 may be provided directly adjacent to the LCD screen 148 for user control of one or more device functions. For instance, a "sleep" button 150 may be provided to access or select and/or deselect a "sleep mode" power setting, while another button may be provided which is, for example, a dispense button 152. While color coded buttons are specifically described, alternative devices may also be implemented, such as, but not limited to buttons having text, buttons having texture differences, pressure-sensitive switches, rocker switches, touch screen interface(s), and combinations of the foregoing. Additionally, in the illustrated embodiment, the respective buttons are located beside the LCD screen 148; however, variations thereon would not depart from the overall scope of the present invention. The device also contains an electronic accelerometer and 3-axis gyroscope in electronic communication with the microprocessor 104 (see FIG. 15).

Figure 15:
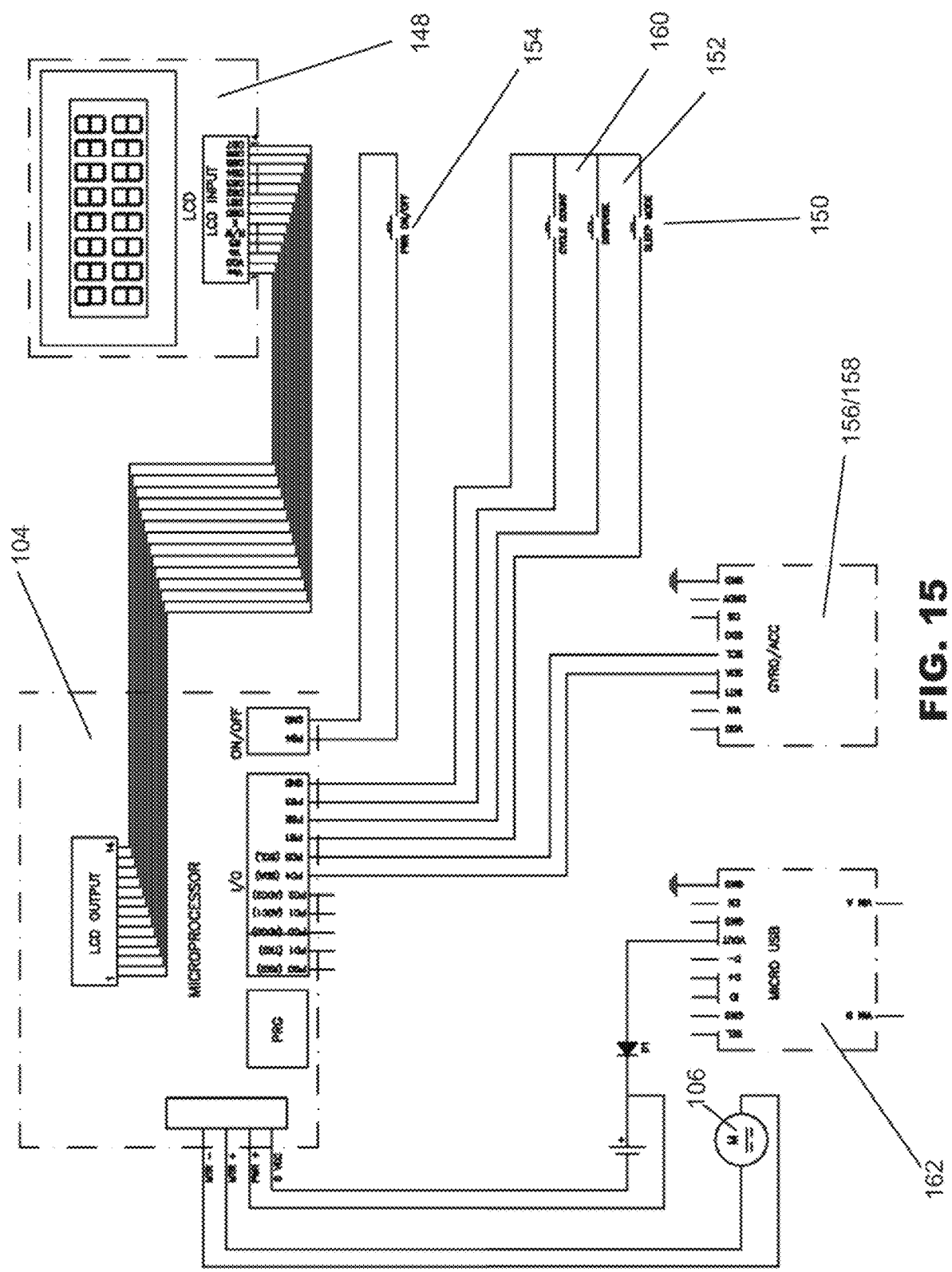
FIG. 15 is a circuit diagram of the dispenser device of FIG. 1, according to one or more examples of embodiments.

FIG. 15 shows a circuit diagram of the automated pill dispenser 100 according to one or more examples of embodiments. As can be seen, the automated pill dispenser 100 has a microprocessor 104 which is electrically coupled to the motor 106 of the automated pill dispenser 100 for control thereof. Also electrically coupled to the microprocessor 104 through an I/O circuit is a gyroscope 158, an accelerometer 156, a cycle count button or switch 160, a dispense button 152, and a sleep mode button 150. The power button or switch 154 and battery 128 are also electrically coupled to the microprocessor 104. A micro-USB charger 162 is, likewise, linked to the microprocessor 104 and battery 128. Lastly, the LCD display screen 148 is electrically coupled to the microprocessor 104, such that output from the microprocessor 104 is input in to the LCD screen 148 for display. While a specific example is provided, it is understood that variations on the circuit arrangement of the automated pill dispenser 100 and variations on the type and number of components therein may be provided without departing from the overall scope of the present invention.

While not specifically illustrated, in one or more examples of embodiments, one or more switches may also be provided on or in the dispenser cap 136. In this regard, the dispensing device may alert the physician upon the patient's opening and access to a medication (e.g., pill 120) dispensed. Furthermore, a switch may be used to validate that the dispenser cap 136 is on the housing 102 before the dispensing device 100 dispenses medication, such as for example, to prevent the patient from inadvertently dropping and/or losing the dispensed medication.

Remote monitoring of the device's actuation, dosage and frequency of allowable use is monitored and controlled by an administration portal. In addition to monitoring of one or more, or all of the above features, two-way communication between the device and the administrator via a cellular or other wireless signal may also be provided to allow an administrator the ability to adjust any of the device parameters remotely and receive real-time feedback on its use. Accordingly, the dispensing device 100 may also include one or more remote components. That is the dispensing device 100 communicates with a third party communications host which houses one or more of the functions of the dispensing device. To this end, in one or more examples of embodiments, the dispenser device 100 and remote or third party host each have a means to receive and transmit a wireless signal. In this regard, the dispenser device 100 and/or remote host are provided with a wireless adapter or like component, and may connect to a wireless network. In one or more examples of embodiments, the dispenser device/remote host is a Bluetooth enabled device. Accordingly, the device 100 and/or remote host may include a transceiver chip which transmits and receives an acceptable frequency band. Alternatively or additionally, the dispenser device 100 and/or remote host may include a near field communication device. Near field communication may be used alone or in combination with Bluetooth or Wi-Fi. Encryption and verification may also be provided, regardless of the form of wireless communication. While wireless communication is described herein, including specific examples, variations thereon would not depart from the overall scope of the present invention including, for example, wired communications. One or more of the foregoing components may be in communication with the microprocessor for interaction with the dispensing device.

The wireless communication device permits the dispenser 100 to pair with the third party remote host. As a result, some or all of the administration software and other components may be housed separately from the dispensing device.

As indicated herein, dispensing medication using the dispenser device 100 is accomplished and controlled in conjunction with the use of administration software. Generally, the dispenser device 100 is a stand-alone dispensing unit with enough onboard intelligence to react to a dispensing command within the limits of preset onboard parameters. In one or more particular examples of embodiments, all of the parameters and settings needed to control the dispensing process are stored onboard the dispenser device 100 in the digital memory of its microprocessor control. However, in alternative embodiments, less than all of the parameters and settings needed to control the dispensing process may be stored onboard the dispenser device 100, in which case they may be stored on the third party host or other remote data storage system.

It is also possible for the dispensing parameters to be altered remotely via a third party host. In this regard, in order for the dispensing parameters to be altered, the dispenser device 100 must be "paired" to its third party host and information sent to the host from an administrator. Alternatively, it is contemplated that one or more dispensing parameters may be altered directly on the dispenser device 100. Parameter manipulation and adjustment is controlled by administration software and, in the case of the remote system described above, uploaded to the dispenser device 100 via the third party host, as commanded by the administrator.

The parameters may remain resident on the dispenser device 100 until such time(s) as a command to update data is received from the administrator via the third party host. Alternatively, parameters may be delivered in real time. In the event of a loss of signal between the dispenser device 100 and the third party host, the device may act as a stand-alone unit dispensing within the limits of the parameters last uploaded and stored on the device.

In one or more examples of embodiments, a microprocessor 104 has instructions for how many cycles are to be dispensed. The microprocessor 104 may perform this determination by use of initial dispensing data. Accordingly, in one or more examples of embodiments, the dispenser device 100 has initial dispensing data. The initial dispensing data comprises a data packet. The data packet consists of integers that populate preconfigured set point fields and form the basis of the dispensing criteria. A variety of dispensing criteria may be used and may be contemplated by one of skill in the art in a manner suitable for the intended purposes. As a non-limiting example, the device may be preconfigured to consider one (1) cycle to constitute one (1) pill dispensed a total of one (1) time. The dispensing criteria, accordingly, may contain the number of cycles required per dispensing event, as well as the number of times an event can be executed. Alternative or additional criteria, such as a lapsed time period, and the like, may be used without departing from the overall scope of the present inventions.

Accordingly, the microprocessor 104 monitors the total number of cycles (e.g. using the cycle count switch) and decrements the count from a value stored in memory. The count may be associated with the amount of medicine, the amount of doses, amount of doses available or remaining, and other suitable parameters. As the contents of the device (e.g., medicine 120) are depleted, the count reduces. Set points may be provided or available or set to trigger one or more messages back to the third party host to alert the host of the incident of achieving a set point—e.g., a low set point achieved—as well as count totally depleted, or other incidents or factors of concern. In one or more examples of embodiments, the count may be reset or increased (for example, by a physician or pharmacist) if the dispenser device 100 is refillable.

The execution of each event is also controlled by the data packet. The number of events deployable within a given time frame may be controlled, as well as the total number of events allowable between reloading of the data from the third party host. As indicated, in one or more examples of embodiments, if the device is not paired with the third party host, a total number of events may be allowed or limited in keeping with the pre-loaded criteria or parameters. Once the total number of dispensing events has been deployed, the device may await instruction from the third party host. If pairing is not re-established and a new data packet uploaded, the device may enter a low power hibernation mode until re-paired or until the batteries are depleted. Charging and recharging of the device will maintain the hibernation mode indefinitely.

In one or more examples of embodiments, the dispenser device 100 has three power states, although fewer or more than three power states may also be acceptable for the intended purposes. For instance, the power states include "power on" (and "off"), "sleep mode" and "low power hibernation". Power on is the operational power mode. Sleep mode is a standby mode designed to conserve battery power, but maintain a full state of readiness. Low power hibernation is an ultra-low power condition designed to provide sufficient power to maintain the device's ability to receive a wireless signal. Low power hibernation should not be confused with sleep mode-which retains a state of readiness. For example, the device may be programmed to enter sleep mode if left uninterrupted for a period of time (for example, but not limited to, three minutes or longer). Awakening from sleep mode is accomplished by simply rotating the device about its vertical axis (x') or by depressing a button 150 or 152 located on the control interface 146.

As indicated, in one or more examples of embodiments the dispenser device 100 and third party host, the system of dispensing medication, and/or method may be implemented by a computer system or in combination with a computer system. The computer system and/or dispensing device may be or include a processor. The computer systems may be portable electronic devices for use with the methods and various components described herein and may be programmable computers which may be special purpose computers or general purpose computers that execute the system according to the relevant instructions. The computer system or portable electronic device can be an embedded system, a personal computer, notebook computer, server computer, mainframe, networked computer, workstation, handheld computer, as well as now known or future developed mobile devices, such as for example, a personal digital assistant, cell phone, smartphone, tablet computer, and the like. Other computer system configurations are also contemplated for use with the communication system including, but not limited to, multiprocessor systems, microprocessor-based or programmable electronics, network personal computers, minicomputers, smart watches, and the like. Preferably, the computing system chosen includes a processor suitable in size to efficiently operate one or more of the various systems or functions or attributes of the system and devices described.

The system or portions thereof may also be linked to a distributed computing environment, where tasks are performed by remote processing devices that are linked through a communication network(s). To this end, the system may be configured or linked to multiple computers in a network including, but not limited to, a local area network, wide area network, wireless network, and the Internet. Therefore, information, content, and data may be transferred within the network or system by wireless means, by hardwire connection, or combinations thereof. Accordingly, the servers described herein communicate according to now known or future developed pathways including, but not limited to, wired, wireless, and fiber-optic channels.

Data may be sent or submitted via the Internet, wireless, and fiber-optic communication network(s), or created or stored on a particular device. In one or more examples of embodiments, data, such as but not limited to, instructions, parameters, analytic or usage data may be stored. In one or more examples of embodiments, data may be stored remotely or may be stored locally on a user's device. In one example, data may be stored locally in files, such as but not limited to, data stored by an app. However, data may also be stored remotely and retrieved. Locally created content or data may also be used and stored.

Data may be stored and transmitted by and within the system in any suitable form. Any source code or other language suitable for accomplishing the desired functions described herein may be acceptable for use.

Furthermore, the computer or computers or portable electronic devices may be operatively or functionally connected to one or more mass storage devices, such as but not limited to, a database. The memory storage can be volatile or non-volatile, and can include removable storage media. Cloud-based storage may also be acceptable. The system may also include computer-readable media which may include any computer-readable media or medium that may be used to carry or store desired program code that may be accessed by a computer. The invention can also be embodied as computer-readable code on a computer-readable medium. To this end, the computer-readable medium may be any data storage device that can store data which can be thereafter read by a computer system. Examples of computer-readable medium include read-only memory, random-access memory, CD-ROM, CD-R, CD-RW, magnetic tapes, flash drives, as well as other optical data storage devices. The computer-readable medium can also be distributed over a network-coupled computer system so that the computer-readable code is stored and executed in a distributed fashion.

The portable electronic device, software system and communication interface further operate and integrate with a user's personal computer. In one or more examples of embodiments, a user's personal computer may act or operate as a "server" storing one or more data files (e.g., parameters) for use by the software system and communication interface. The personal computer may also utilize an Internet-connected website, provided to manage one or more functions of the software system and communication interface operated by the portable electronic device. In other words, the portable electronic device, software application, communication interface, personal computer, and website may be integrated for use.

The computer or portable electronic device or the communication interface (e.g., LCD screen 148) can also include a display, provision for data input and output, etc. For example, these devices include a graphical user interface (GUI) or a communication means by which commands may be entered and content may be displayed or communicated. The computer or portable electronic device includes a user interface that allows navigation of objects. The computer or portable electronic device implements or includes an application that enables a user to display and interact with communications.

Aspects of the method described herein are implemented on a software system running on a computer system. To this end, the methods and system may be implemented in, or in association with, a general purpose software package or a specific purpose software package.

The software system described herein may include a mixture of different source codes. The system or method herein may be operated by computer-executable instructions, such as but not limited to, program modules, executable on a computer. Examples of program modules include, but are not limited to, routines, programs, objects, components, data structures, and the like which perform particular tasks or implement particular instructions. The software system may also be operable for supporting the transfer of information within a network.

In one or more examples of embodiments, the system described herein, and/or portions thereof, may be implemented in a web-based platform or website platform or a device application ("app") platform, or a combination or integration of web and mobile app or application platform or structure. The software application may be, for example, a mobile device app having an integrated website. In one particular example of a mobile application, the system may operate within a closed-loop server system. In this example, the application and a linked website integrate with closed-loop servers using supporting source code. Any source code capable of supporting the functions described herein may be suitable for the purposes provided. The servers may facilitate the storage of data or content (e.g., parameters described herein), and synchronize the application and web content libraries, in/out message boxes, push notifications, software updates, and other data and/or features, such as user usage analytics and the like. The portable electronic devices or Internet-connected devices also communicate with the servers to exchange the referenced data, including the transfer of data associated with each message created by the system.

An integrated file system may also be provided which allows users or administrators to manage, select, create, and import content or data. Various examples of file structures and categories are acceptable for use with the integrated file system.

Figure 16:
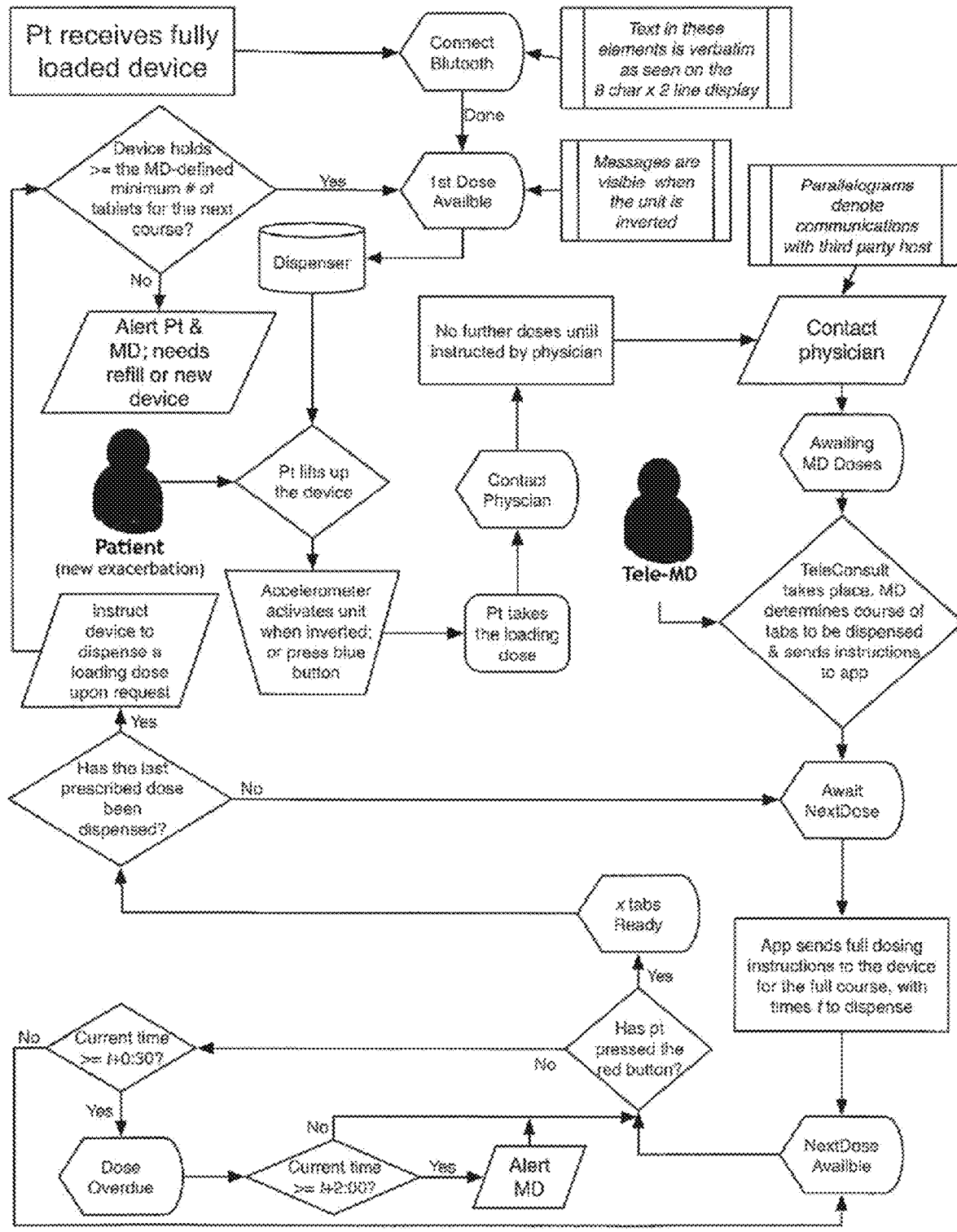
FIG. 16 is a logic diagram of the method and system of dispensing medication using the dispenser device according to one or more examples of embodiments.

Referring to FIG. 16, a logic diagram illustrating the operation of the administration software is provided. After a patient receives a fully loaded (e.g., loaded with medication) dispenser device, the device initially connects or pairs with Bluetooth. Once paired, the software from the third party host communicates the availability of the first dose to the dispenser device. In one or more examples of embodiments, the software may count the total number of doses of medication available and dispensed based upon a predetermined load and analysis of the actions of the dispensing device. A message is also displayed on the communication interface identifying the availability of a dose. When a patient lifts the dispenser device (e.g., when a patient is experiencing a new exacerbation), the accelerometer activates the dispenser device. In the alternative, the depression of a button on the communication interface activates the dispenser device. If the dispensing button is pressed, the defined loading dose (e.g., physician defined loading dose) is dispensed. The software may display "loading dose." Once a successful dispensing sequence has been completed by the device, it may report to the third party host with an output noting "process complete" or "process incomplete" (in the event of an error). The patient takes the loading dose, a message is displayed to contact the physician, and no further doses are permitted until instructed by the physician. The physician is contacted, and a consult occurs, such as but not limited to a telephone consult, in which the physician determines the course of medicine to be dispensed. Simultaneously, no further doses are permitted. The physician provides instructions to the third party host, namely, to the administration software. In the interim, the dispenser device may display "awaiting physician doses", "awaiting next dose", or the like. Upon receipt of instructions, the software application sends full dosing instructions to the device for the full course, with one or more times to dispense medication. The dispenser device then displays that the next dose is available. If the next dose is available, the system queries whether the dispense button has been depressed. If the button is depressed, then the dispenser device is operated to deliver or dispense x-number of pills or a predetermined quantity of medication and the amount is displayed on the device screen. If the dispense button has not been depressed at the time the next dose is available, then the system queries whether the current time is greater than a first preset dispensing time (for example, time "t"+30 minutes). If this parameter has not been met, then the next dose remains available and this message continues to be displayed for the patient. If the current time has exceeded the first preset dispensing time, a message is displayed to the patient that a dose is overdue. In one or more examples of embodiment, the software may deliver periodic push notifications to the user until it receives a message from the dispenser that the does has been delivered. The system then queries whether the current time is greater than a second preset dispensing time (for example, time "t"+2 hours). If this parameter has not been met, the system cycles to query whether the patient has pressed the dispense button again, and subsequently the first preset dispensing time. If the second preset dispensing time has been exceeded, the system alerts the physician and, again, cycles to query whether the patient has pressed the dispense button. If the patient presses the dispense button and medicine is dispensed, then the system queries whether the last prescribed dose has been dispensed. If not, the system cycles to await the next dose. If the last prescribed dose has been dispensed, then instructions are sent to the device to dispense a loading dose upon request. The dispenser device holds greater than or equal to the defined minimum amount of medication (e.g., number of pills or tablets) for the next course. This defined minimum may be set, for example, by the physician via the third party host. If this parameter is met, the first dose is then made available and cycle repeats. If the minimum is not met the dispenser device alerts the physician—through the third party host, of a need for a refill or a new device.

Accordingly, the foregoing describes an automated medication dispenser system. The automated medication dispenser system generally includes a dispenser device comprising a medication dispensing and storage module, a dispensing drive and control mechanism, and a communications interface. The communications interface may include a screen and one or more control buttons. The system also includes a third party communications host in communication with the dispenser device, and has administration software with executable instructions for control of the dispensing drive and control mechanism to dispense medication from the medication dispensing and storage module. The executable instructions may include dose quantity and dose time. The communications interface is in communication with the third party communications host. In one or more examples of embodiments, the dispenser device may also comprise localized control software required to perform independent dispensing operations. In one or more examples of embodiments, the dispenser device may also include a gyroscope and accelerometer for monitoring an orientation of the dispenser device.

One or more examples of operation of the dispenser device 100 will now be described in reference to the Figures for purposes of illustration.

The dispenser device 100 is pre-loaded and sealed with a pre-determined amount of medicine 120. Once the device has been loaded and deployed to a user, it is turned on via the discrete momentary contact 154. This provides power to the microprocessor 104 from, for example, the onboard rechargeable battery pack 128. The device may be powered up at all times and remain powered up indefinitely. Alternatively, the device may be powered "on-call."

Upon powering on the device, a series of startup messages may be displayed via the LCD screen 148. The microprocessor 104 is initialized and the device 100 pairs with its third party host. If pairing for the first time, messages may be provided to guide the user through the initial setup. Once successfully paired, the device receives its initial dispensing data. As indicated, the initial dispensing data is provided as a data packet which may consist of integers that populate preconfigured set point fields and form the basis of the dispensing criteria. The dispensing criteria may contain the number of cycles required per dispensing event, as well as the number of times an event can be executed.

The execution of each dispensing event is also controlled by the data packet. In one or more examples of embodiments, the number of events deployable within a given time frame is controlled. The total number of dispensing events allowable between reloading of the data from the third party host may also be controlled. If the device is not paired with the host, a total number of events may be allowed or limited in keeping with the pre-loaded criteria.

Once the total number of dispensing events has been deployed, the device will await instruction from the third party host. If pairing is not re-established and a new data packet uploaded, the device may enter a low power hibernation mode until re-paired or until, for example, the battery is depleted. To this end, charging and/or recharging of the device may maintain the hibernation mode indefinitely.

As indicated, the dispenser device 100 contains an electronic accelerometer 156 and 3-axis gyroscope 158. Accordingly, the device's axial position and its state of rest are constantly monitored, regardless of its power state. For example, the accelerometer 156 may sense motion and alert the microprocessor 104 to enter the "Power On" mode (if not already transferred into this mode). In one or more examples of embodiments, in order to actuate a dispense cycle, the device must be in the "Power On" mode. The gyroscope 158 senses the axial position of the dispenser device 100 relative to its environment. In one or more preferred examples of embodiments, in order for the device to be able to successfully dispense, the device 100 must be inverted so as to align the dispensing housing's main axis in a vertical position. In this position, not only is the main axis (x') vertically positioned, but the face containing the LCD screen 148 and interface buttons are facing up (see FIG. 7). The gyroscope 158 confirms this alignment and may inhibit any actuation (and thus medicine dispensing) until correct alignment is achieved. Once oriented correctly and the power status is in the "Power On" mode, the device is available for dispensing.

Depressing a button 152 on the control interface 146 may commence a dispensing sequence in keeping with the data stored on the device at that time. Once a dispensing sequence is received, the microprocessor 104 determines how many cycles are to be dispensed. The microprocessor 104 enables the DC gear motor 106 to start operation. The motor 106 actuates, rotating pinion gear 110 which, in turn, rotates internal gear 112 and the dispensing plate 114. The holes in the dispensing plate 114 momentarily align with cavities in the pill holder 118 as the dispensing plate 114 rotates. As indicated, pill silos 122 are arranged in a circular configuration about the dispenser plate's axis of rotation.

Spring pressure, from the compression spring and spring seat 124 located at the base of each pill silo 122, is exerted on the base of each pill silo 122 forcing an entire column of pills 120 in the pill silo 122 in the direction of the dispensing plate 114. Rotation of the dispensing plate 114 aligns the plate's aperture or cavity with a pill silo 122, and spring force (assisted by gravity) inserts a pill into a vacant aperture in the dispensing plate 114. Once the aperture or cavity is populated, the resident pill inhibits additional silos 122 from loading into that particular aperture or cavity as the populated cavity is rotated about the respective silos 122.

The populated aperture or cavity continues to rotate until it aligns with a hole located in the motor mounting flange 108. Referring to FIGS. 10-12, during the rotation, the cycle count switch is depressed by a cam (i.e., the cycle count cam lobe 144) located on the dispensing plate each time a cavity passes the unloading point. The cam 144 is positioned to coincide with each hole or aperture of the dispensing plate as it arrives at the unloading point. The cycle count switch 160 is depressed once every time a cam lobe (and coinciding cavity) passes by, thus providing a cycle count to the microprocessor during actuation. Gravity, assisted by the hole's geometry, allows the pill to fall freely through the motor mounting flange 108 and continue through a feed chute 130 located in the battery housing 126, finally passing through the retaining plate 132 and coming to rest in the chamber located between the retaining plate 132 and the dispenser cap 136. The cycle count cam lobe 144 further assists the evacuation of the pill through the motor mounting flange 108 as it passes through the center of the cavity during the rotation cycle. The dispenser cap 136 may then be removed to retrieve the dispensed pill 120.

One or more specific examples of use of the dispenser 100 will now be described for purposes of illustration. One of skill in the art would understand that variations thereon would be acceptable without departing from the overall scope of the present invention.

The patient stores the dispenser device 100 in a location in keeping with their needs. In the event that the patient needs to access medication, the patient begins retrieving the device, inverting it to orient the dispenser 100 in a vertical plane with the LCD screen 148 facing up (FIG. 7). If the device is not in the "Power On" mode (signified by an on screen message on the LCD screen 148), the patient has the option of either lightly moving the device to awaken it or pressing an activation button 154 or the sleep button 150 momentarily.

Once the device is in "Power On" mode, the patient can depress an "actuate" or "dispense" button 152. The device 100 will then actuate and dispense the quantity of medicine as set forth in the data packet. The LCD screen 148 may display a message, such as the message "Dispensing," while in operation. Once dispensing is complete the LCD screen 148 may, likewise display a message, such as, but not limited to "Dose Available" or the like. The patient can now retrieve the dose by opening the dispenser cap 136.

Accordingly, the foregoing describes a method for control and monitoring the dosing of medication. The method generally includes connecting a dispenser device with a third party host, and once paired, automatically communicating the availability of a dose of medication to the dispenser device. Depression of a button on a communication interface may activate the dispenser device, or upon lifting of the dispenser device, an accelerometer activates the dispenser device. Following loading of the dose of medication, the loading of additional doses of medication may be restricted without additional dosing instructions. Dosing instructions are communicated with the involvement of the third party host. For example, request for further dosing instructions is communicated to a third party host. Upon receipt of dosing instructions from the third party host, dosing instructions are sent to the dispenser device. Dispensing of medication from the device may occur, in one or more examples of embodiments, only when the dispense button is depressed. Accordingly, the process further includes querying whether a dispense button has been depressed and operating the dispenser device to deliver a predetermined quantity of medication according to the dosing instructions, as well as counting the dispensation of the medication. The method also may comprise the step of simultaneously displaying a message on a communication interface of the dispensing device. A current time may be queried relative to one or more preset dispensing times. Additionally, the method may include sending an alert to a third party host.

The dispenser device described herein provides various advantages of existing methods of identification and treatment, as well as control of medication dosing and use. A mechanism to monitor and control of the dispensation of medication is also provided. Moreover, the dispensing device having the features described herein provides improved means to determine and use pharmacy data on the use of medication, such as oral steroids. In addition, the device allows for additional interventions that would further reduce the patent's risk for further exacerbations.

While the device is described herein for use with the dispensation of pills, and in one or more examples of embodiments in reference to the assessment of oral corticosteroid use associated with asthma, the invention is not limited thereto. One of skill in the art would understand that the use in association with OCS use for asthma is merely one of many examples by which a physician, pharmacist, insurance company, patient, and others may monitor, control, and dispense medication. Likewise, one of skill in the art would appreciate the alternative forms of medication apart from pills may be used with the inventions described herein.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that references to relative positions (e.g., "top" and "bottom") in this description are merely used to identify various elements as are oriented in the Figures. It should be recognized that the orientation of particular components may vary greatly depending on the application in which they are used.

For the purpose of this disclosure, the term "coupled" means the joining of two members directly or indirectly to one another. Such joining may be stationary in nature or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It is also important to note that the construction and arrangement of the system, methods, and devices as shown in the various examples of embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts and vice versa, the operation of the interfaces may be reversed or otherwise varied, the length or width of the structures and/or members or connectors or other elements of the system may be varied, the nature or number of adjustment positions provided between the elements may be varied (e.g., by variations in the number of engagement slots or size of the engagement slots or type of engagement). The order or sequence of any process or method steps may be varied or re-sequenced according to alternative embodiments. Other substitutions, modifications, changes and omissions may be made in the design, operating conditions and arrangement of the various examples of embodiments without departing from the spirit or scope of the present inventions.

While this invention has been described in conjunction with the examples of embodiments outlined above, various alternatives, modifications, variations, improvements and/or substantial equivalents, whether known or that are or may be presently foreseen, may become apparent to those having at least ordinary skill in the art. Accordingly, the examples of embodiments of the invention, as set forth above, are intended to be illustrative, not limiting. Various changes may be made without departing from the spirit or scope of the invention. Therefore, the invention is intended to embrace all known or earlier developed alternatives, modifications, variations, improvements and/or substantial equivalents.

The technical effects and technical problems in the specification are exemplary and are not limiting. It should be noted that the embodiments described in the specification may have other technical effects and can solve other technical problems.

The invention claimed is:

1. A patient-handled automated medication dispenser device communicable with a communications host, the dispenser device comprising:
   a medication dispensing and storage module for storing and dispensing medication including a loading dose and at least one continuing treatment dose;
   a dispensing drive and control mechanism for dispensing the medication;
   a communications interface for communicating with the communications host;
   a processor and a memory having localized control software with instructions executable by the processor to:
      receive a patient-initiated activation of the dispenser device to dispense the loading dose of the medication;
      cause the dispensing drive and control mechanism to dispense the loading dose from the dispenser device based on receiving the activation;
      following dispensing the loading dose, cause the dispenser device to
         restrict dispensing of any continuing treatment doses without additional dosing instructions,
         communicatively connect with the communications host,
         communicate to the communications host the dispensing of the loading dose, and
         receive additional dosing instructions from the communications host, with input of a supervising medical provider; and
      following receiving the additional dosing instructions, cause the dispenser device to
         allow dispensing of one or more continuing treatment doses based on the additional dosing instructions received,
         receive a second patient-initiated activation of the dispenser device to dispense continuing treatment dose(s) of the medication, and
         cause the dispensing drive and control mechanism to continue dispensing treatment dose(s) based on receiving the second activation and the additional dosing instructions received.

2. The dispenser device of claim 1, wherein the localized control software includes instructions further executable by the processor to
   prior to dispensing the loading dose, cause the dispenser device to display availability of the loading dose, and
   following receiving the additional dosing instructions, cause the dispenser device to display a continuing treatment dose is available.

3. The dispenser device of claim 1, wherein the receiving a patient-initiated activation of the dispenser device includes receiving an actuation of a button on the dispenser device.

4. The dispenser device of claim 1, wherein the localized control software includes instructions further executable by the processor to
   following dispensing the loading dose and prior to receiving the additional dosing instructions, cause the dispensing device to display a message to contact the supervising medical provider for additional dosing instructions for the dispensing device.

5. The dispenser device of claim 1, wherein the localized control software includes instructions further executable by the processor to
   following receiving the additional dosing instructions, cause the dispenser device to alert the host if a dose has not been taken at a prescribed time.

6. The dispenser device of claim 1, wherein the localized control software includes instructions further executable by the processor to
   following receiving the additional dosing instructions, cause the dispenser device to alert a supervising medical provider via the host if a dose has not been taken at a prescribed time.

7. The dispenser device of claim 1, wherein the localized control software includes instructions further executable by the processor to
   prior to dispensing the loading dose, communicatively connect the dispenser device with the host device, and the dispenser device receive communication from the host device regarding availability of the loading dose.

8. The dispenser device of claim 1, wherein the dispensing the continuing treatment dose(s) of the medication includes operating the dispenser device to deliver a quantity of medication according to the dosing instructions and counting delivery of a predetermined quantity of medication towards the additional dosing instruction.

9. The dispenser device of claim 1, wherein the localized control software includes instructions further executable by the processor to
   following dispensing the loading dose and prior to receiving the additional dosing instructions, the dispenser device receiving a third input to dispense a continuing treatment dose of the medication; and
   wherein restricting the dispensing of any continuing treatment dose includes preventing the dispensing of the continuing treatment dose even though the third input was received and the dispenser device includes the at least continuing treatment dose.

10. A communications host for an automated medication dispenser system having a plurality of dispenser devices, wherein at least one of the plurality of dispenser devices comprises a medication dispensing and storage module for storing and dispensing medication including a loading dose and at least one continuing treatment dose, a dispensing drive and control mechanism for dispensing the medication, and a communications interface communicable with the communications host, the communications host comprising a processor and a memory having administration software with instructions executable by the processor to:
   communicatively connect with the at least one dispenser device;
   receive communication that the at least one dispenser device dispensed the loading dose of the medication;
   communicatively connect with a supervising medical provider;
   communicate to the supervising medical that the at least one dispenser device dispensed the loading dose of the medication;
   receive input from the supervising medical provider with additional dosing instructions; and
   communicate to the at least one dispenser device to allow dispensing of one or more continuing treatment doses based on the received additional dosing instructions.

* * * * *